(12) United States Patent
Ferrero

(10) Patent No.: US 7,317,018 B2
(45) Date of Patent: Jan. 8, 2008

(54) ANTI-INFLAMMATORY MEDICAMENT

(75) Inventor: Maria Elena Ferrero, Milan (IT)

(73) Assignee: Medestea Internazionale S.p.A., Turin (IT)

( * ) Notice: Subject to any disclaimer, the term of this patent is extended or adjusted under 35 U.S.C. 154(b) by 377 days.

(21) Appl. No.: 10/343,756

(22) PCT Filed: Jul. 26, 2001

(86) PCT No.: PCT/EP01/08643

§ 371 (c)(1),
(2), (4) Date: Aug. 29, 2003

(87) PCT Pub. No.: WO02/11737

PCT Pub. Date: Feb. 14, 2002

(65) Prior Publication Data

US 2004/0023920 A1    Feb. 5, 2004

(30) Foreign Application Priority Data

Aug. 4, 2000   (IT) ............................ MI2000A1827

(51) Int. Cl.
*A61K 31/52* (2006.01)
*C07F 9/113* (2006.01)
(52) U.S. Cl. .................................... 514/263.4; 544/244
(58) Field of Classification Search ............ 514/263.4
See application file for complete search history.

(56) References Cited

U.S. PATENT DOCUMENTS 5,847,135 A * 12/1998 Bemis et al. ................ 544/264
6,096,728 A *  8/2000 Collins et al. ................ 514/62

OTHER PUBLICATIONS

Easterbrook-smith et al., (1976) Eur. J. Biochem. vol. 62, pp. 125-130.*
Pearce et al., Eur. J. Biochem. vol. 88, pp. 543-554, (1978).*
Hu et al., Journal of Biological Chemistry, vol. 273(42), pp. 27170-27175, 1998.*
Woolf et al., "Neuropathic pain: aetiology, symptoms, mechanisms, and management" (1999) The Lancet, vol. 353, pp. 1959-1964.*
Laliberte et al. "Tenidap Modulates Cytoplasmic pH and Inhibits Anion Transport In Vitro" (1994) J. Immunology, vol. 153, pp. 2168-2179.*

Ferrari et al. "Purinergic Modulation of Interleukin-1β Release from Microglial Cells Stimulated with Bacterial Endotoxin" (1997) J. Exp. Med. vol. 185, No. 3, 579-582.*
Murgia et al. "Oxidized ATP: An irreversible inhibitor of the Macrophage Purinergic P2z Receptor" (1993) J. Biol. Chem. vol. 268, No. 11, pp. 8199-8203.*
The Merck Manual of Diagnosis and Therapy, Seventeenth Edition, Published by Merck Research Laboratories (1999) Beers and Berkow, eds., pp. 1373, 1374, and 1511.*
XP-001056870, J. Org. Chem., 1982, O'Donnell et al., "A Mild and Efficient Router to Schiff Base Derivatives of Amino Acids", pp. 2663-2666.
XP-001056970, Drug Development, 1998, Di Virgilio et al., "Purinergic P2X$_7$ Receptor: a Pivotal Role in Inflammation and Immunomodulation", pp. 207-213.
XP-002191118, American Physiological Society, 1998, Schulze-Lohoff et al., "Extracellular ATP causes apoptosis and necrosis of cultured mesangial cells via P2Z/P2X$_7$ receptors", pp. F962-F979.
XP-002191119, Journal of Biological Chemistry, 1998, Hu et al, "Purinergic Receptor Modulation of Lipopolysaccharide Signaling and Inducible Nitric-oxide Synthase Expression in RAW 264.7 Macrophages", pp. 27170-27175.
XP-002191120, Journal of Neuroscience, 2000, Liu et al., "Modulation of Interleukin-1β and Tumor Necrosis Factor α Signaling by P2 Purinergic Receptors in Human Fetal Astrocytes", pp. 5292-5299.
XP-002191121, American Association of Immunologists, 1999, Mutini et al., "Mouse Dentritic Cells Express the P2X$_7$ Purinergic Receptor: Characterization and Possible Participation in Antigen Presentation[1]", pp. 1958-1965.
XP-002191122, Journal of Cell Science, 1999, Solini et al., "Human primary fibroblasts in vitro express a purinergic P2X$_7$ receptor coupled to ion fluxes, microvesicle formation and IL-6 release", pp. 297-305.
XP-002191123, American Association of Immunologists, 1999, Sikora et al., "Cutting Edge: Purinergic Signaling Regulates Radical-Mediated Bacterial Killing Mechanisms in Macrophages Through a P2X$_7$-Independent Mechanism", pp. 558-561.
XP-001061622, Virology, 1991, Pizarro et al., "Effect of Nucleotide Analogues on rotavirus Transcription and Republication", pp. 768-772.

* cited by examiner

*Primary Examiner*—Shaojia Anna Jiang
*Assistant Examiner*—Eric S Olson
(74) *Attorney, Agent, or Firm*—Young & Thompson

(57) ABSTRACT

The use of adenosine-5'-triphosphate-2',3'-dialdehyde (oATP) as a medicament useful for the treatment of inflammatory conditions is disclosed.

11 Claims, 3 Drawing Sheets

FCA - treated paw

Untreated paw

FCA          Diclofenac and oATP injection

ANTI-INFLAMMATORY MEDICAMENT

Figure 1:
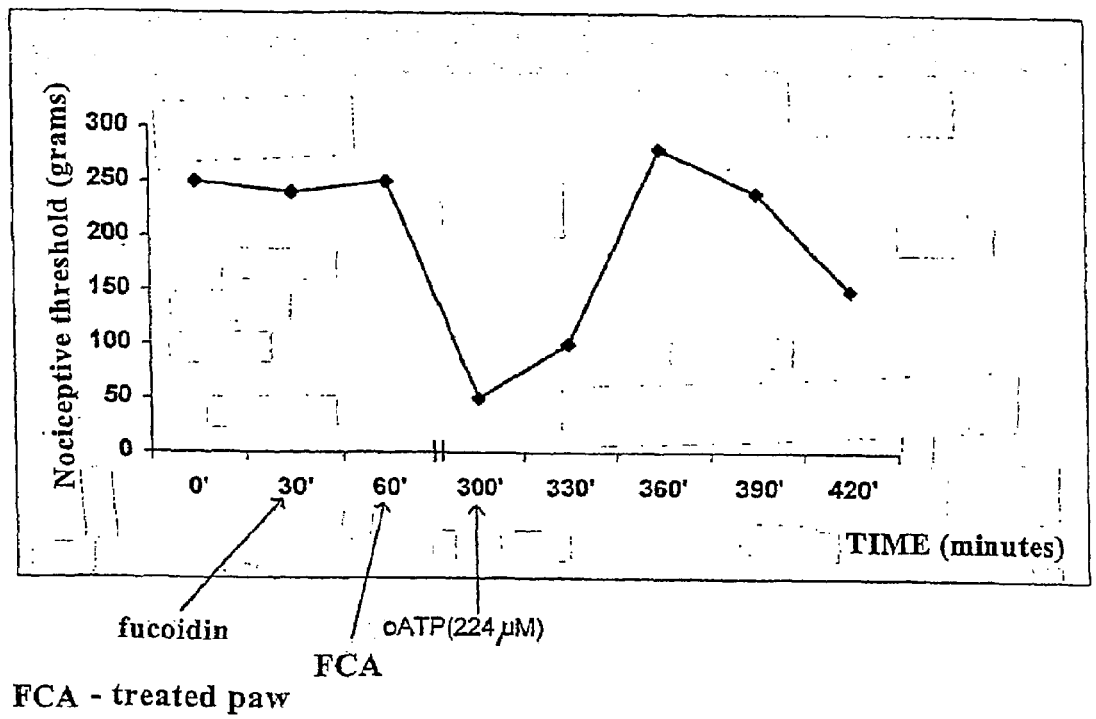
Figure 1:
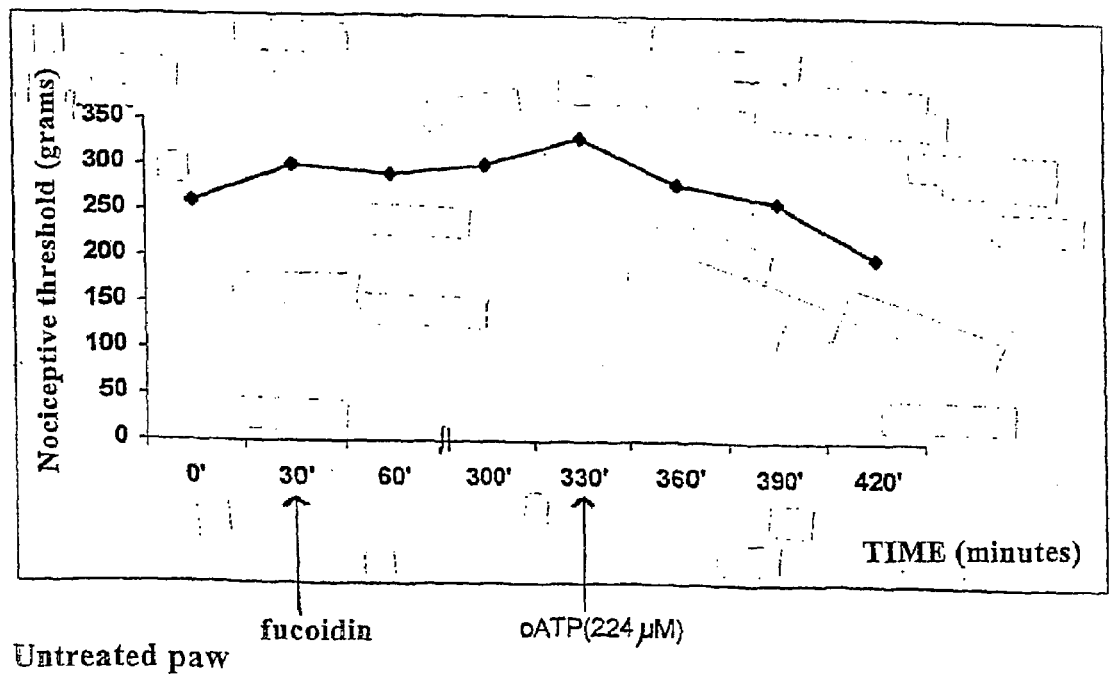

This application is a national stage application of PCT/EP01/08643, filed Jul. 26, 2001, which claims priority to foreign application IT MI2000A001872, filed Aug. 4, 2000.

The present invention relates to the use of adenosine-5'-triphosphate-2',3'-dialdehyde (oATP) in the preparation of medicaments useful for the treatment of inflammatory conditions.

The oATP molecule derives from ATP by oxidation of the hydroxyls present at the ribose 2'- and 3' positions to dialdehydes. Such an oxidation can be carried out with a periodic acid salt, as described in P. N. Lowe et al., "Preparation and chemical properties of periodate-oxidized adenosine triphosphate and some related compounds", Biochemical Society Transactions, Vol. 7:1131-1133, 1979.

ATP 2',3'-dialdehyde derivative is traditionally used as affinity marker for enzymatic nucleotidic sites (Easterbrook-Smith, B., Wallace, J. C. & Keech, D. B. (1976) Eur. J. Biochem. 62, 125-130), because it is capable of reacting with the lysine unprotonated residues present in the nucleotidic sites to form Schiff bases or dihydromorpholino derivatives (Colman, R. F. (1990) in The Enzymes—Sigman, D. S., and Boyer, P. D., eds—Vol 19, pp. 283-323, Academic Press, San Diego). The oATP molecule has also been used to study platelet activation and inhibit stimulation of chicken skeletal muscle by ATP (Pearce, P. H., Wright, J. M. Egan. C. M. & Scrutton, M. C. (1978) Eur. J. Biochem. 88, 543-554; Thomas, S. A., Zawisa, M. J., Lin, X. & Hume, R. I. (1991) Br. J. Pharmacol. 103, 1963-1969). Furthermore, studies on macrophage cell lines proved that oATP is able to block the plasmatic membrane permieabilisation effect induced by ATP, to reduce the hydrolysis level of exogenous ATP by membrane ecto-ATPases and to inhibit the swelling, vacuolisation and cellular lysis effects induced by ATP (Murgia et al. The Journal of Biological Chemistry, (1993) by The American Society for Biochemistry and Molecular Biology, inc., Vol. 268, No. 11, pp 8199). oATP has been suggested to have antagonistic activity on P2z/P2X7 purinoceptors. IL-1β (interleukin 1β) LPS (=lypopolysaccharide)—dependant release from microglial cells expressing P2z/P2X7 is in fact selectively inhibited by oATP (Ferrari D. et al., J. Exp. Med., (1997) Vol. 185, N. 3, Pag. 579-582).

It has now been found that oATP exerts in vivo remarkable anti-inflammatory and antinociceptive effects. As experimental model, a unilateral inflammation in rat hind paw, after intraplantar injection of Freund's complete adjuvant (FCA), has been used. The controlateral paw of treated animals, as well as that of untreated animals, were used as controls. Inflammation induced by FCA was evidenced, from 3 h until 24-48 h following injection, by increase in paw volume, hyperthermia and hyperalgesia. The latter was evaluated by an algesyometric test (paw pressure test) capable of evaluating the nociceptive threshold. Intraplantar injection of oATP significantly reduced pain sensing (nociception), i.e. it increased nociceptive threshold. Different doses of oATP always induced a significant, dose-dependent analgesic effect, lasting approximately 12-24 hours, with an effect peak already one hour after the administration. Furthermore, paws of oATP-treated rats showed reduction of the other inflammatory signs (swelling and hyperthermia). In a further test, comparison between oATP and diclofenac, a known anti-inflammatory drug used in arthritic pathologies, proved that oATP induces a significantly higher analgesic effect than diclofenac. A test in which rats were pre-treated with fucoidin, a leukocyte diapedesis inhibitor, showed that oATP activity is independent of leukocyte recruitment at the inflammation site. ATP levels at the inflammation sites were significantly higher in untreated animals, which suggests that oATP may somewhat block exogenous ATP production, thus preventing its pro-inflammatory activity.

The present invention relates to the use of oATP as medicament for the treatment of inflammatory and pain conditions. The invention further relates to pharmaceutical compositions containing oATP as active ingredient, together with pharmaceutically acceptable excipients. Suitable forms for the oral, topical or parenteral administrations are, for example, tablets, sugar coated pills, capsules, granulates, powders, suppositories, syrups, solutions, suspensions, creams, ointments, gels, pastes, lotions, emulsions, spray. The pharmaceutical compositions can be prepared according to what described in Remington's Pharmaceutical Sciences Handbook, Mack Pub. Co., NY, USA, XVII Ed. The amount of active ingredient per unitary dosage may range from 0.05 to 100 mg per Kg body weight, to be administered once or more times daily, depending on the severity of the disease to be treated and the conditions of the patient. The daily dosage will usually range from 1 to 300 mg, preferably from 10 to 100 mg.

The compound of the invention may also be used in combination with other currently used anti-inflammatory drugs.

The following example further illustrates the invention.

EXAMPLE 1 oATP Pharmacological Activity

Induction of Inflammation in Rats

Male Fischer inbred rats (Charles River Italy, Calco, Lecco, Italy) weighing about 250 g were used. Rats, under brief isoflurane anaesthesia received an intraplantar injection of Freund's complete adjuvant (FCA) (0.15 ml) into the right hind paw. This injection induced a unilateral inflammation (from 3 h until 24-48 h following injection) evidenced by increase in paw volume, hyperthermia and hyperalgesia. Hyperalgesia was assessed by an algesyometric test, using an analgesyometer (Ugo Basile, Comerio, Italy) to determine the paw pressure threshold, expressed in grams, namely the pressure required to elicit paw withdrawal, which indicates the nociceptive threshold value. 6 to 8 rats were used for each test. During these trials, animals were treated according to the "standard ethical guidelines" (NIH, 1985).

Treatment with oATP

Rat inflamed paw received, 24 hrs after FCA injection, intraplantar injection of different doses of oATP (56 to 336 μM), considering time 0 the moment of oATP injection. The nociceptive threshold values obtained are reported in the following Table 1.

TABLE 1

| NOCICEPTIVE THRESHOLD OR "PAW PRESSURE THRESHOLD" | | | |
|---|---|---|---|
| OATP 56 μM | 112 μM | 224 μM | 336 μM |
| 0'   60 ± 1.6 | 65 ± 2.0 | 50 ± 1.5 | 60 ± 1.9 |
| 30'  120 ± 2.1* | 140 ± 3.5* | 350 ± 54* | 300 ± 3.4* |
| 60'  190 ± 2.3* | 180 ± 4.2* | 400 ± 10.3* | => 750 *1 |
| 90'  85 ± 2.5* | 150 ± 3.8* | 300 ± 11.2* | => 750 *2 |
| 120' 75 ± 1.8* | 100 ± 3.0* | 185 ± 7.1* | 600 ± 20.8* |
| 240' 75 ± 2.6* | 105 ± 4.3* | 180 ± 8.9* | 550 ± 18.4* |

*1.2 = cut off
Data are expressed as mean ± S.E.M. of paw pressure threshold (evaluated in g) p < 0.05 vs. time 0' (untreated inflamed paw)
*Mann-Whitney test.

Similar results were obtained using oATP 35 μm in place of oATP 56 μm or inducing the inflammatory process (FCA injection) for 6 or 12 h instead of 24 h. Furthermore, oATP treated paws were less painful and also showed reduction of inflammatory signs (swelling, hyperthermia) compared with untreated paws.

A dose-dependent effect of oATP was evidenced, although already significantly high effects were attained at the minimal dose used. Lower doses had however a less lasting analgesic effect in time, possibly due to incomplete saturation of P2X7 receptors.

The effect of the maximal oATP dose used was tested in a further set of experiments, for more prolonged times, on rat paws in which the inflammatory process had been induced 48 hrs before (table 2). The data prove that oATP njection significantly increases nociceptive threshold values for an exceedingly long time, although progressively decreasing in time.

TABLE 2

NOCICEPTIVE THRESHOLD OR "PAW PRESSURE THRESHOLD

| | OATP 336 μM. |
|---|---|
| 0' | 55 ± 2.0 |
| 30' | 210 ± 10.7 |
| 60' | 360 ± 25.8 |
| 90' | 395 ± 30.2 |
| 120' | 450 ± 38.1 |
| 180' | 550 ± 45.9 |
| 240' | 690 ± 56.6 |
| 12 hours | 400 ± 29.7 |
| 24 hours | 210 ± 7.2 |
| 26 hours | 190 ± 3.3 |

The nociceptive threshold values of the control paws (both noninflamed controlateral and untreated paws) were approximately 100-150, expressed as nociceptive threshold or paw pressure threshold and evaluated in g.

Intraplantar injection of ATP (0.9 mmoles) (extracellular ATP is cytolytic and therefore possibly able to initiate a nociceptive signal) induced reduction of nociceptive threshold significantly higher in noninflamed paws than in inflamed paws (values of 120±3.2 to 25±3.0 found in noninflamed paws, 240' after intraplantar injection of ATP) in comparison with a decrease from 65±4.2 to 50±4.1 in inflamed paws. This result possibly indicates that cytolytic ATP is already present in higher amounts in inflamed paws than in noninflamed ones. On the other hand, oATP was effective in increasing nociceptive threshold, for a short time, also in noninflamed paws, being already effective at the lowest oATP concentration (=56 μM). Dose/effect curves in noninflamed paws were in fact superimposable (until 120' after oATP administration) using different concentrations of the molecule. In order to ascertain whether oATP analgesic effect was somewhat related to the activation of inflammatory cells able to produce endogenous β-endorphins, some rats were intravenously injected with fucoidin (10 mg/kg). Fucoidin in fact inhibits leukocyte diapedesis and their accumulation at the inflammation site. Pre-treatment with fucoidin was carried out in both paws, 30' before FCA injection in one of the rat paws. Pain pressure threshold (PPT) was measured in both noninflamed and inflamed paws, before and after oATP injection (224 μm). The obtained results are reported in the graphics of FIG. 1. oATP injection did not significantly change PPT values in noninflamed paws, while in inflamed paws oATP treatment restored PPT levels which had been severely reduced by the injection of pro-inflammatory FCA. oATP analgesic effect was therefore independent of leukocyte recruitment.

Figure 2:
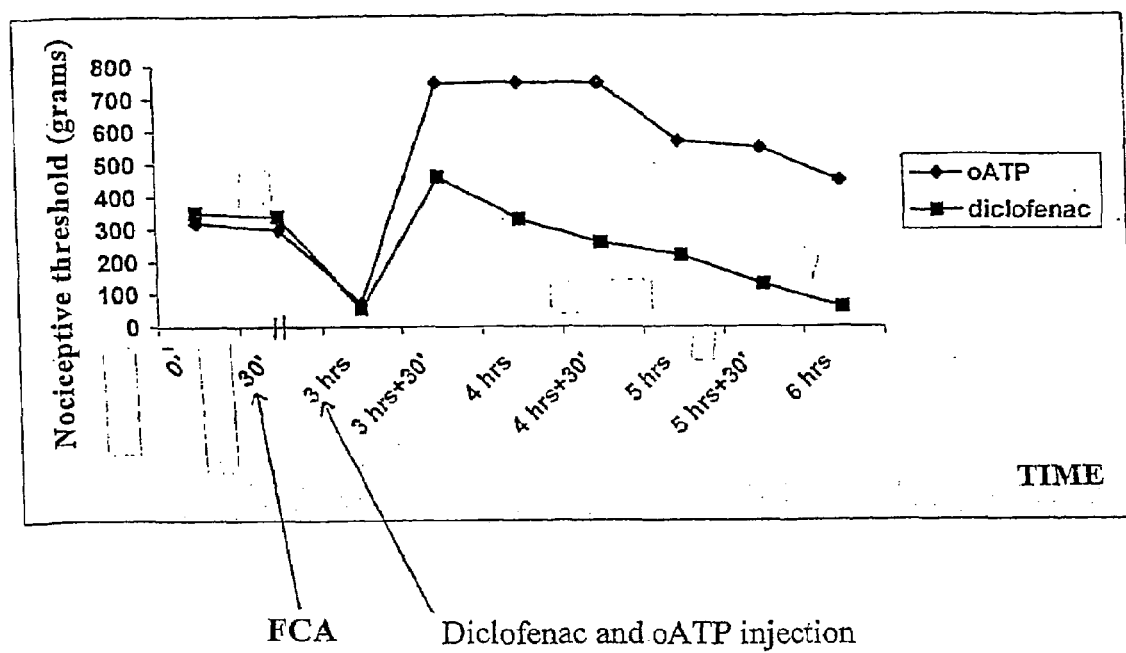

Finally, oATP antinociceptive efficacy was compared with that of a known anti-inflammatory and analgesic drug, diclofenac. After evaluation of the basal pain threshold, unilateral inflammation of the hind paw of rats was induced by FCA injection. 3 Hours after the injection, animals were divided in 2 groups, which were treated locally one with oATP (336 μM) and the other with diclofenac (15 mg). oATP analgesic efficacy was significantly higher than that of diclofenac (results of a typical trial are reported in FIG. 2). oATP and diclofenac concentrations were selected as to allow good dissolution of the molecule in sterile saline, before the intraplantar injection in rats.

Finally, intravenous injection of oATP in rats, at the tested intraplantar doses, induced dose-dependent pain relief for approximately two hours, although reflex were apparently still present.

ATP content was assessed in oATP treated rat paws and controlateral untreated ones. Paw subcutaneous tissues were removed from both inflamed and noninflamed paws and rapidly frozen in liquid nitrogen. The frozen tissue samples were weighed, homogenised in phosphate buffer, then treated with $K_2CO_3$ and neutralised, finally centrifuged. The supernatant was used for ATP assay, following the luminescence method.

ATP values were significantly higher in homogenates from untreated paws than in OATP treated paws (1050±90 nmoles/g fresh tissue in untreated animals, vs. 320±22 nmoles/g fresh tissue in oATP treated animals—each value is the mean±S.E.M. of 7 experiments). This indicates that oATP blocks the production of exogenous ATP by some tissular structure, binding to its membrane receptors, thereby reducing the damage induced by exogenous ATP.

EXAMPLE 2

Modification of ATP Content in Peripheral Subcutaneous Tissue Following oATP Treatment Assay of ATP Content in Rat Paw.

We determined in a separate group of rats the modifications in ATP content induced in the plantar tissue by the inflammatory process and/or by oATP treatment. At established times, paw subcutaneous tissues were removed and rapidly frozen in liquid nitrogen, with the aim of blocking any metabolic activity. The frozen tissue was homogenized with a polytron (Kinematica GmbH, Luzern, Switzerland) in ice-cold 6% (w/v) $HClO_4$ to extract nucleotides. The homogenate was centrifuged and the supernatant was used for ATP determination, following the procedure previously described (Marni et al., Transplantation (1988), 46: 830-835). ATP assay was performed by luminescence method (Ferrero et al., Res Commun Chem Path Pharmac 1984; 45: 55-67).

Results

We measured ATP levels, in inflamed (by 24 h FCA treatment) and noninflamed paws treated with oATP, at 6 and 12 h following oATP administration, and in controlateral untreated paws. As reported in FIG. 3, in noninflamed tissues oATP treatment did not significantly change ATP levels: the data could express the intracellular levels of the metabolite, which is not significantly modified by oATP treatment. On the contrary, the levels of ATP in inflamed tissues, significantly higher than in non inflamed tissues, were significantly reduced by oATP treatment. In fact the release of ATP (extracellular ATP) from cells requires their damage and occurs during inflammatory or other degenerative processes. The binding of oATP with the receptors localized on many cells and also on sensory nerve terminals could competitively block the binding of extracellular ATP to the same structures, so limiting ATP-related cytotoxicity and inducing pain relief. Our results indicate also that oATP treatment in inflamed tissues limits further production of ATP by inflammatory or other cells possibly through a block of their activation.

Figure 3:
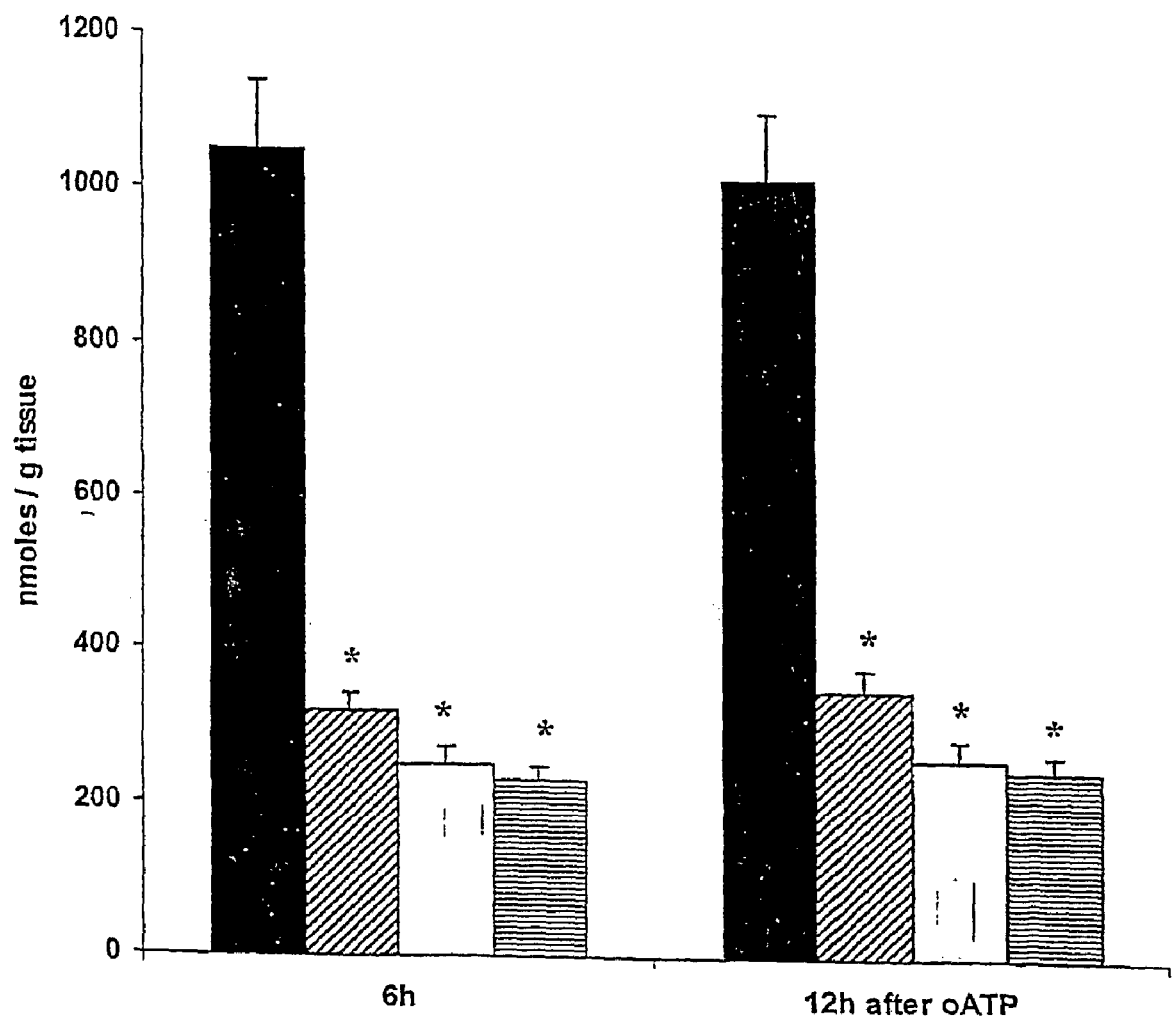

FIG. 3: Effect of oATP Intraplantar Injection on ATP Levels of Inflamed or Noniniflamed Paws.

ATP content, at 6 and 12 h following intraplantar oATP (35 µM) injection in rat paws: inflamed (by 24 FCA administration) (filled bars), inflamed-oATP treated (hatched bars), noninflamed (open bars), noninflamed-oATP-treated (horizontal line bars). *$p<0.005$ compared with inflamed untreated paws, Wilcoxon test. Data are expressed as means±S.E.M. of 7 experiments.

The invention claimed is:

1. A method for treating inflammation or nociceptive pain in a subject, comprising:
    administering to said subject an effective amount of adenosine-5'-triphosphate-2',3'-dialdehyde.

2. The method according to claim 1, wherein the adenosine-5'-triphosphate-2',3'-dialdehyde is in the form of an oral, topical, or parenteral administration.

3. The method according to claim 2, wherein the adenosine-5'-triphosphate is administered in the form of a tablet, sugar-coated pills, capsules, granulates, powders, suppositories, syrups, solutions, suspensions, creams, ointments, gels, pastes, lotions, emulsions, and spray.

4. The method according to claim 1, further comprising administering adenosine-5'-triphosphate-2',3'-dialdehyde in a daily dosage of 1 to 300 mg per dosage.

5. The method according to claim 1, wherein said dosage is 10 to 100 mg.

6. The method according to claim 1, wherein the adenosine-5'-triphosphate-2',3'-dialdehyde is in a dosage form of 1 to 300 mg.

7. A method for treating inflammation or pain in an inflamed tissue in a subject, comprising:
    administering to said subject an effective amount of adenosine-5'-triphosphate-2',3'-dialdehyde.

8. The method according to claim 7, wherein the adenosine-5'-triphosphate-2',3'-dialdehyde is in the form of an oral, topical, or parenteral administration.

9. The method according to claim 8, wherein the adenosine-5'-triphosphate is administered in the form of a tablet, sugar-coated pills, capsules, granulates, powders, suppositories, syrups, solutions, suspensions, creams, ointments, gels, pastes, lotions, emulsions, and spray.

10. The method according to claim 7, wherein said adenosine5'-triphosphate-2',3'-dialdehyde is administered in a daily dosage of 1 to 300 mg per dosage.

11. The method according to claim 10, wherein said dosage is 10 to 100 mg.

* * * * *